United States Patent [19]

Gong

[11] Patent Number: 5,512,430
[45] Date of Patent: Apr. 30, 1996

[54] DIAGNOSTIC ARRAY FOR VIRUS INFECTION

[75] Inventor: Yu Gong, Concord, Calif.

[73] Assignee: HRI Research, Inc., Concord, Calif.

[21] Appl. No.: 91,234

[22] Filed: Jul. 13, 1993

[51] Int. Cl.$^6$ .............................. C12Q 1/70; C12Q 1/68;
C12P 19/34; C07H 17/00
[52] U.S. Cl. .............................. 435/5; 435/6; 435/91.32;
435/91.33; 435/974; 536/24.33; 935/1;
935/16; 935/19; 935/20; 935/77
[58] Field of Search .............................. 435/5, 6, 91.32,
435/91.33, 974; 536/24.33; 935/1, 16, 19,
20, 77

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 4,889,818 | 12/1989 | Gelfand et al. | 435/194 |
| 5,196,305 | 3/1993 | Findlay et al. | 435/6 |
| 5,310,893 | 5/1994 | Erlich | 536/24.31 |

OTHER PUBLICATIONS

Vogel et al., *Virology*, vol. 154, No. 2, pp. 335–343, Oct. 30, 1986.
Higuchi, Chapter 4, *PCR Technology*, 1989, H. A. Erlich, ed., pp. 31–38.
S. Crowe et al., "Infections of the Immune System," In Basic and Clinical Immunology, 7th Ed. (1991) (D. P. Stites and A. I. Terr, Eds.) pp. 697–711.
L. Ratner et al., "Complete Nucleotide Sequence of the AIDS Virus, HTLV–III," Nature 313:277 (1985).
M. Popovic et al., "Detection, Isolation, and Continuous Production of Cytopathic Retroviruses (HTLV–III) from Patients with AIDS and Pre–AIDS," Science 224:497 (1984).
F. Barin et al., "Virus Envelope Protein of HTLV–III Represents Major Target Antigen for Antibodies in AIDS Patients," Science 228:1094 (1985).
C. Ou et al., "DNA Amplification for Direct Detection of HIV–1 in DNA of Peripheral Blood Mononuclear Cells," Science 239:295 (1988).
J. Bell et al., "Specificity of Polymerase Chain Amplification Reactions for Human Immunodeficiency Virus Type I DNA Sequences," AIDS Res. Hum. Retrovir., 5:87 (1989).
R. Higuchi, "Simple and Rapid Preparation of Samples for PCR," In PCR Technology (1989) (H. A. Erlich, Ed.) pp. 31–38.
*Guidelines for Prevention of Transmission of HIV and HBV to Health–Care and Public Safety Workers*, CDC (Feb. 1989).
Resnick et al., "Stability and Inactivation of HTLV–III/LAV Under Clinical and Laboratory Environments," JAMA 255:1887 (1986).
H. Arnold et al., In Andrews' Disease of the Skin, pp. 9–10 (W. B. Saunders Co., Philadelphia, PA, 1990).

H. Spiegel et al., "Follicular Dendritic Cells are a Major Reservoir for Human Immunodeficiency Virus Type 1 in Lymphoid Tissues Facilitating Infection of CD4$^+$ T–helper Cells," Rapid Communication Amer. J. Pathol., 140:15 (1990).
E. Tschachler et al., "Epidermal Langerhans Cells—A Target for HTLV–III/LAV Infection*," J. Invest. Dermatol., 88:233 (1987).
G. Stingl et al., "Langerhans Cells in HIV–1 Infection," J. Amer. Acad. Dermatol., 22:1210 (1990).
J. Leonard et al., "The Human Immunodeficiency Virus Long Terminal Repeat is Preferentially Expressed in Langerhans Cells in Transgenic Mice," AIDS Res. Human Retro., 5:421 (1989).
G. Zambruno et al., "Detection of HIV–1 in Epidermal Langerhans Cells of HIV–Infected Patients Using the Polymerase Chain Reaction," J. Invest. Dermatol., 96:979 (1991).
A. Giannetti et al., "Direct Detection of HIV–1 RNA in Epidermal Langerhans Cells of HIV–Infected Patients," J. Acquired Immune Defic. Syndr., 6:329 (1993).
C. Cruickshank et al., "Pigment Donation In Vitro*," J. Invest. Dermatol., 42:183 (1964).
R. Higuchi et al., "DNA Typing from Single Hairs," Nature 332:543 (1988).
N. Arnhelm et al., "Polymerase Chain Reaction," Chem. Eng. News., Oct. 1, p. 36 (1990).
R. Uchihi et al., "Deoxyribonucleic Acid (DNA) Typing of Human Leukocyte Antigen (HLA)–DQA–1 from Single Hairs in Japanese," J. Forensic Sci., 37:853 (1992).
D. Kacian et al., "A Replicating RNA Molecule Suitable for a Detailed Analysis of Extracellular Evolution and Replication," Proc. Nat. Acad. Sci. USA 69:3038 (1972).
M. Chamberlin et al., "New RNA Polymerase from *Escherichia Coli* Infected with Bacteriophage T7," Nature 228:227 (1970).
D. Wu et al., "The Ligation Amplification Reaction (LAR)—Amplification of Specific DNA Sequences Using Sequential Rounds of Template–Dependent Ligation," Genomics 4:560 (1989).
R. Saiki, "The Design and Optimization of the PCR," In PCR Technology (1989) (H. A. Erlich, Ed.) pp. 7–16.
Perkin Elmer Cetus Biotechnology Catalog, "GeneAmplimer HIV Primers and Probe," 1991.
Sigma, St. Louis, MO, U.S.A., Catalogue No. p4914 "Proteinase K."M. Piatak, Jr., et al., "High Levels of HIV–1 in Plasma During All Stages of Infection Determined by Competitive PCR," Science 259:1749 (1993).
A. Jeffreys et al., "Amplification of Human Minisatellites by the Polymerase Chain Reaction: Towards DNA Fingerprinting of Single Cells," Nucl. Acids Res., 16:10953 (1988).

*Primary Examiner*—W. Gary Jones
*Assistant Examiner*—Bradley L. Sisson
*Attorney, Agent, or Firm*—Medlen & Carroll

[57] ABSTRACT

The use of nucleic acid to diagnose disease is disclosed. The use of nucleic acid from at least one hair follicle to diagnose the presence of a human immunodeficiency virus infection is demonstrated.

14 Claims, 3 Drawing Sheets

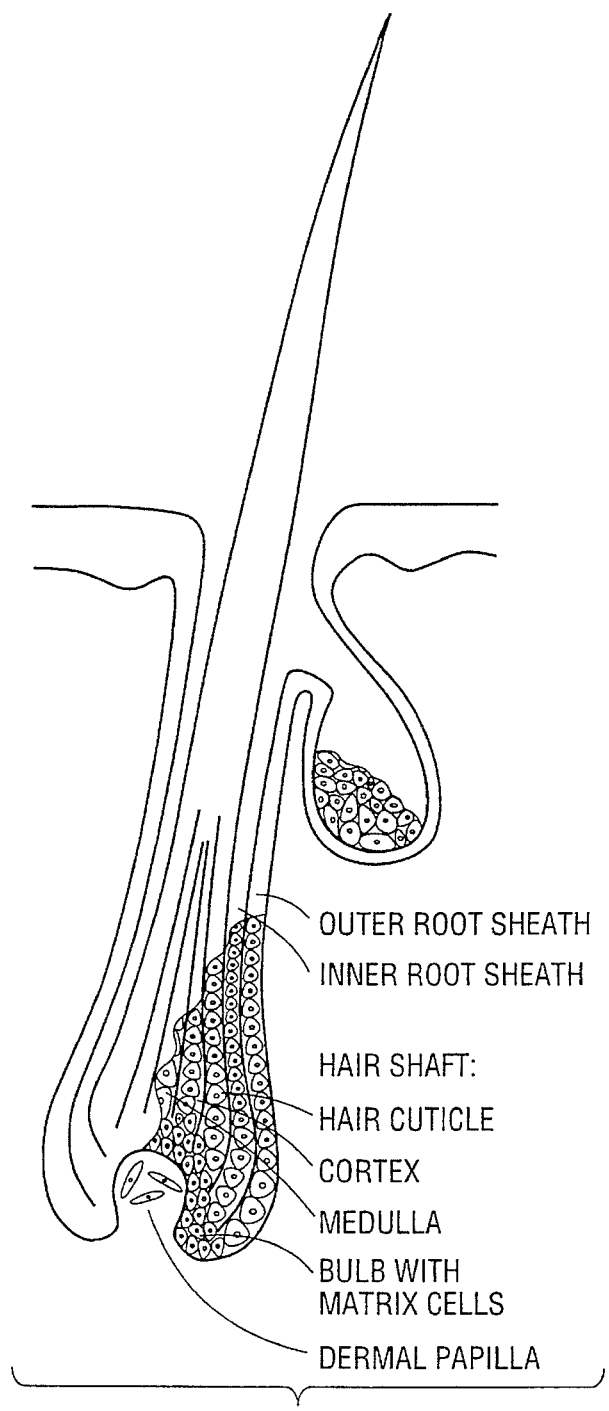
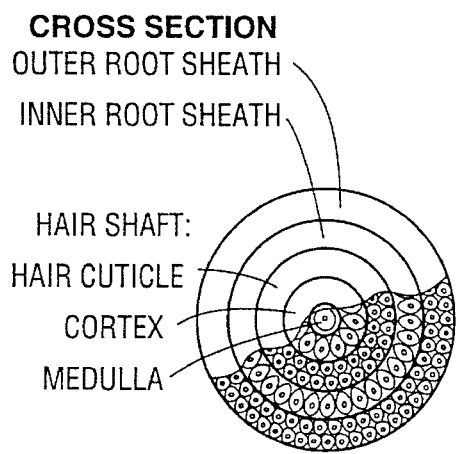
FIG. 1A
FIG. 1B

SK38    5'-ATAATCCACCTATCCCCAGTAGGAGAAAT-3'

SK39    5'-TTTGGTCCTTGTCTTATGTCCAGAATGC-3'

115-mer 5'-ATAATCCACC TATCCCCAGTA GGAGAAATTT
           ATAAAAGATG GATAATCCTG GGATTAAATA
           AAATAGTAAG AATGTATAGC CCTACCAGCA
           TTCTGGACAT AAGACAAGGA CCAAA-'3

SK19    5'-ATCCTGGGATTAAATAAAATAGTAAGAATGTATAGCCCTAC-3'

FIG. 2

DIAGNOSTIC ARRAY FOR VIRUS INFECTION

FIELD OF THE INVENTION

The present invention relates to the use of nucleic acid to diagnose disease, and in particular the use of nucleic acid from cells to diagnose viral disease.

BACKGROUND OF THE INVENTION

An ever-increasing number of viruses are being identified as the source of human disease. The better known virally-caused diseases include chicken pox, measles, mumps, influenza, hepatitis, poliomyelitis, rabies, and now, of course, Acquired Immunodeficiency Syndrome (AIDS).

Human immunodeficiency virus (HIV) is the etiologic agent of AIDS. See S. Crowe and J. Mills in *Basic and Clinical Immunology*, 7th Ed. (D. P. Stites and A. I. Terr, Eds.), pp. 697–711 (1991) at p. 697, col. 1. A complete sequencing of the HIV genome indicates that it comprises the same overall gag-pol-env organization as other retroviruses. See L. Ratner et al., *Nature* 313:277 (1985) at p. 277, Abstract. The virus invades a host cell and uses the host cell's machinery to replicate itself.

HIV infects cells that have a protein called CD4 on the cell surface. CD4 serves as a receptor for the virus. Lymphoid cells susceptible to infection include $CD4^+$ T lymphocytes, monocyte-macrophages, dendritic cells, and Langerhans cells. In addition, HIV can infect non-lymphoid microglial cells, retinal cells, colonic mucosal cells, and endothelial cells, all of which have the CD4 surface antigen. See S. Crowe and J. Mills in *Basic and Clinical Immunology*, 7th Ed. (D. P. Stites and A. I. Terr, Eds.), pp. 697–711 (1991) at p. 699, col. 1.

The monocyte-macrophage cells are probably the first cells infected by HIV. Viral replication proceeds slowly in these cells, with little cytopathology, and the cells apparently become a major reservoir for the virus. See S. Crowe and J. Mills in *Basic and Clinical Immunology*, 7th Ed. (D. P. Stites and A. I. Terr, Eds.), pp. 697–711 (1991) at p. 697, col 1. In contrast, when HIV invades $CD4^+$ lymphocytes, it replicates more rapidly and, through a mechanism that is not completely understood, causes depletion of the circulating $CD4^+$ lymphocyte population.

The detection of HIV in human peripheral blood cells is now well-documented. The first assays involved isolation and culture of the virus. See M. Popovic et al., *Science* 224:497 (1984) at p. 497, Abtract. However, the process takes 3–4 weeks and has low sensitivity. Subsequent assays measured anti-viral antibody produced by human immune cells that contacted the virus. See F. Barin et al., *Science* 228:1094 (1985) at p. 1094. While this is a faster technique, it is an indirect method of detection, measuring past exposure to the virus, not present infection. Finally, direct detection of viral DNA sequences was achieved by amplification techniques such as the Polymerase Chain Reaction (PCR). See C. Y. Ou et al., *Science* 239:295 (1988) at p. 295 Abstract. See also J. Bell and L. Ratnet, *AIDS Res. Hum. Retrovir.* 5:87 (1989) at p. 87, Abstract.

PCR was developed by K. B. Mullis et al., U.S. Pat. Nos. 4,683,195 and 4,683,202. PCR provides a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to a sequence on their respective strands of the double stranded target sequence. To effect amplification, the mixture is denatured and the primers are then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. Because the desired amplified segments of the target sequence become the predominant sequences (in terms of concentration) in the mixture, they are said to be "PCR amplified."

With PCR, it is possible to amplify a single copy of a specific target sequence present in genomic DNA to a level which is detectable by several different methodologies (e.g., hybridization of PCR-amplified sequences with a labelled probe; incorporation of biotinylated primers followed by avidin-enzyme conjugate detection; incorporation of $^{32}P$-labelled deoxynucleotide triphosphates, e.g., dCTP or dATP, into the amplified segment). In addition to specific sequences present in genomic DNA, any oligonucleotide sequence, including HIV sequences, can be amplified with an appropriate set of primer molecules.

Using blood cells as a source of DNA, HIV sequences have been amplified sufficiently to be detected by hybridization probes. See C. Y. Ou et al., *Science* 239:295 (1988) at p. 295, col 2. However, the application of this method for detecting HIV in a general population has drawbacks. Blood cells and serum contain inhibitors of PCR. See R. Higuchi in PCR Technology, Principles and Applications for DNA Amplification (H. A. Erlich, Ed.), pp. 31–38 (1989). To avoid inhibition, the nucleic acid from blood cells typically must be isolated and purified prior to amplification, a step that results in a loss of sensitivity. Furthermore, only about 1 in 10,000 $CD4^+$ lymphocytes express viral RNA in HIV-infected individuals. See C. Y. Ou et al., Science 239:295 (1988) at p. 295, col 2. See also S. Crowe and J. Mills in *Basic and Clinical Immunology*, 7th Ed. (D. P. Stiles and A. I. Terr, Eds.), pp. 697–711 (1991). The concentration of the HIV sequence is thus very low in comparison to total cellular sequences and low copy number is associated with additional problems in the execution of the PCR technique.

For low copy number systems, such as the presence of HIV sequence in human cells, one typically needs a larger sample size (e.g., many cells) in order to be sure the sequence of interest is present in the sample. Large sample sizes, however, have more inhibitor. Furthermore, large samples are not readily amenable to amplification because of the expense of large sample amplification, as well as the inhibiting impact of very large amounts of nucleic acid on most amplification techniques.

The above considerations are best understood by the example of the low copy situation in the case of HIV infection. The number of HIV infected $CD4^+$ T lymphocytes (or T4 cells) can be as low as one out of every 1,000 T4 cells, and only 30% (maximum) of the total white blood cell population are T4 cells. Therefore, for each HIV PCR beginning with 40 infected T4 cells, a minimum of 100–300 μl of normal whole blood will be required. A larger volume may be needed for HIV patients due to depletion of their T4 cells. However, since PCR is normally carried out in 100 μl, a volume reduction step, which allows concentration of white blood cells, may be necessary to avoid the expense of using large amounts of enzyme.

One potential problem of cell concentration steps is that the final amount of DNA obtained by the procedure may be too high for PCR to efficiently proceed. It has been shown that the amount of DNA present in 0.5 ml of normal whole blood is difficult or impossible to amplify all at once by PCR. The occurrence of DNA-dependent PCR inhibition is probably due to an excess of misprimed sites (relative to enzyme molecules), which form unproductive ternary complexes with the polymerase. This results in the accumulation of a large number of linearly or exponentially amplified non-target sequences. Since the specificity of the amplification is lost as the amount of non-target DNA is increased, the exponential accumulation of the target sequence of interest does not occur to any significant degree.

In addition to the PCR-related problems associated with amplifying HIV sequences from blood samples, there are numerous problems associated with drawing blood. Certain persons may object to the invasive aspect of venipuncture. Furthermore, it requires trained personnel to draw and process the blood and this entails additional costs. These factors and the special requirements needed for proper storage of blood make it a less than optimal test method in developing countries and remote areas.

One problem that has received considerable attention is the risk of infection to health workers and pathologists who are involved with testing blood and other biological fluids. The Occupational Safety and Health Administration (OSHA) has issued guidelines on safer handling of contaminated specimens. See Guidelines for Prevention of Transmission of HIV and HBV to Health-Care and Public Safety Workers, CDC (February 1989).

Following the onset of the AIDS epidemic, there has been a renewed desire to reduce exposure of personnel to human blood and body fluid samples. Technologists who come into contact with samples from AIDS patients are aware that an infectious virus can persist in a liquid or dried state for prolonged periods of time, possibly even at elevated temperatures. Resnick et al., *JAMA* 255:1887 (1986) at p. 1887, Abstract.

Thus, there remains a need for a method for detecting HIV infection with speed, sensitivity, and safety. In addition, if the method is to be useful in outlying areas, simplicity of sample collection and storage are required.

SUMMARY OF THE INVENTION

The present invention relates to the use of nucleic acid to diagnose disease, and in particular the use of nucleic acid from cells to diagnose viral disease.

One viral disease contemplated is the human imxnunodeficiency virus (HIV). A cell line (ATCC CRL 8543) is available which produces the virus.

The present invention contemplates, in a preferred embodiment, providing cells suspected of containing a viral nucleic acid sequence from at least one hair follicle and amplifying and detecting that viral nucleic acid sequence. In one embodiment, the method comprises the use of DNA as the viral nucleic acid sequence, including DNA sequences from HIV. In another embodiment, the method comprises the use of RNA as the viral nucleic acid sequence, including RNA sequences from HIV.

The present invention further contemplates detecting HIV infection by providing cells from at least one hair follicle suspected of containing an HIV nucleic acid sequence, lysing those cells to make a lysate containing the nucleic acid, and treating the lysate to amplify the HIV nucleic acid sequence. In one embodiment, the lysing is effected by adding a lysing agent such as a protease and then inactivating the protease.

The present invention further contemplates treating the lysate by providing all standard reagents necessary to amplify at least a portion of the HIV nucleic acid sequence as well as at least one amplification enzyme capable of initiating an amplification reaction resulting in a nucleic acid product; adding the reagents so as to form a reaction mixture; and adding the amplification enzyme to the reaction mixture. In one embodiment, the method comprises the use of *Thermus aquaticus* polymerase as the amplification enzyme.

DESCRIPTION OF THE DRAWINGS

FIG. 1 is a diagram of a hair follicle.

FIG. 2 shows the sequences of the oligonucleotide primer pair SK38 (SEQ ID NO:1)/SK39 (SEQ ID NO:2), the 115-mer target HIV sequence (SEQ ID NO:3), and the SK19 oligonucleotide hybridization probe (SEQ ID NO:4).

DESCRIPTION OF THE INVENTION

Figure 3A:
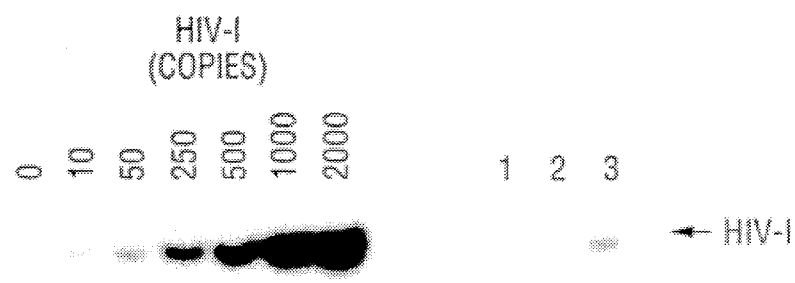
FIG. 3A is an autoradiogram of PCR products following liquid oligomer hybridization with the $^{32}$P-labelled SK19 (SEQ ID NO:4) probe which demonstrates the presence of HIV sequences in the hair root from a HIV seropositive person.

The present invention relates to the use of nucleic acid to diagnose disease, and in particular the use of nucleic acid from human hair follicle cells.

As shown in FIG. 1, hair comprises a hair shaft, with an outer and inner root sheath, and a root. The hair shaft is comprised of hair cuticle, cortex, and medulla. The root of the hair ends in an enlargement, the hair bulb, or hair follicle, which is white and softer than the shaft. H. L. Arnold et al. in *Andrews' Disease of the Skin*, W. B. Saunders Co., Philadelphia, Pa., pp. 9–10 (1990). Hair follicles are implanted in the epidermis.

Part of the epidermal network includes the dendritic Langerhans cells that populate the epidermis and mucosal epithelia. A growing body of evidence indicates that HIV infects the Langerhans cells and affects the skin and mucosa. H. Spiegel et al., *Amer. J. Pathol.* 140:15 (1990); E. Tschachler et al., *J. Invest. Dermatol.* 88:233 (1987) at p. 233 Abstract. G Stingl et al., J. Amer. Acad. Dermatol. 22:1210 (1990); L. Braathen and C. Mork in Skin Langerhans (dendritic) cells in virus infections and AIDS, (Y. Becker, Ed.), Kluwer Academic Publishers, Newell, Mass., pp. 131–39 (1991); J. Leonard et al., *AIDS Res. Human Retro.* 5:421 (1989) at p. 421, Abstract. PCR amplification and detection of HIV-1 proviral DNA in epidermal cells showed that the Langerhans cells are the only epidermal cell type that harbor the virus. G. Zambruno et al., *J. Invest. Dermatol.* 96:979 (1991) at 9. 979, Abstract. The detection of HIV-1 RNA in epidermal Langerhans cells of HIV-infected patients, using PCR technology, indicated that viral replication occurs in these cells. A. Giannetti et al., *J. Acquired Immune Defic. Syndr.* 6:329 (1993) at p. 329, Abstract.

Certain components of the dendritic cells in the skin can be transferred into hair cortex cells by active phagocytosis. C. N. D. Cruickshank and S. A. Harcourt, *J. Invest. Dermatol.* 42:183 (1964) at p. 183, Col. 1. This could be a mechanism for the transfer of HIV nucleic acid sequences, as well.

Mitochondrial and nuclear DNA sequences from the root region of a single human hair, and mitochondrial DNA sequences from a hair shaft have been amplified by PCR and detected. R. Higuchi et al., *Nature* 332:543 (1988) at p. 183, col 1. Since there are many hundreds of copies of mitochondrial DNA per cell, amplification of mitochondrial DNA does not raise problems due to low copy number.

The nuclear DNA sequence that has been amplified and detected from a single human hair is from a polymorphic region of the nuclear human leukocyte antigen (HLA) gene DQA1. R. Higuchi et al., *Nature* 332:543 (1988) at p. 544, FIG. 2; N. Amhelm and C. H. Levenson, *Chem. Eng. News,* Oct. 1, pp. 36–48 (1990) at p.45, col 2 and R. Uchihi et al., *J. Forenic Sci.* 37:853 (1992) at p. 853, Abstract. While the HLA DQA1 gene is a single copy gene, these gene sequences are present in every nucleated cell. In contrast, only cells which are infected with HIV will harbor HIV gene sequences. As pointed out above, only a fraction of cells known to be susceptible to HIV infection appear to be infected. We were therefore surprised to find that we could detect HIV-1 nucleic acid sequences in hair follicle cells.

The present invention provides a method for the detection and quantitation of viral nucleic acid sequences in hair cells. While the preferred source of cells is hair follicle cells, it is not intended that the present invention be limited to this source alone. The present invention contemplates cells from the hair root sheath as well.

The present invention has applicability to diagnosing viral diseases by the amplification and subsequent detection of viral sequences in hair cells. "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be amplified or detected preferentially in the presence of other non-target nucleic acid sequences. Amplification techniques have been designed primarily for the detection of specific target sequences. Template specificity is achieved, in most amplification techniques, by the choice of enzyme. Amplification enzymes are enzymes that, under the conditions in which they are used, will process only specific sequences of nucleic acid in a heterogenous mixture of nucleic acid. For example, in the case of Qβ replicase, MDV-1 RNA is the specific template for the replicase. D. L. Kacian et al., *Proc. Natl. Acad. Sci. USA* 69:3038 (1972) at p.853 Abstract. Other nucleic acid will not be replicated by this amplification enzyme. Similarly, in the case of T7 RNA polymerase, this amplification enzyme has a stringent specificity for its own promoters. M. Chamberlin et al., *Nature* 228:227 (1970) at p.229, col 2. In the case of T4 DNA ligase, the enzyme will not ligate the two oligonucleotides where there is a mismatch between the oligonucleotide substrate and the template at the ligation junction. D. Y. Wu and R. B. Wallace, *Genomics* 4:560 (1989). Finally, Taq polymerase, by virtue of its ability to function at high temperature, is found to display high specificity for the sequences bounded and thus defined by the primers; the high temperature results in thermodynamic conditions that favor primer hybridization with the specific target sequences and not hybridization with non-target sequences. R. K. Saiki in PCR Technology, Principles and Applications for DNA Amplification (H. A. Erlich, Ed.), pp. 7–16 (1989).

Some amplification techniques take the approach of amplifying and then detecting target; others detect target and then amplify probe. Regardless of the approach, the sample containing nucleic acid must be free of inhibitors for amplification to occur at high efficiency.

"Amplification reagents" are defined as those reagents (primers, deoxyribonucleotide triphosphates, etc.) needed for amplification except for nucleic acid and the amplification enzyme. Typically, amplification reagents along with other reaction components are placed and contained in a reaction vessel (test tube, microwell, etc.). Synthetic oligonucleotide primers for HIV-1 are available commercially. See Perkin-Elmer Cetus Biotechnology Catalog, 1991.

The preferred lysing agent is protease K. Protease K is a proteolytic enzyme from *Tritirachium album*. It is particularly useful in the present invention because it has no significant DNase activity and, therefore, does not degrade nucleic acid which would prevent amplification. It is also attractive because it is inexpensive and commercially available (e.g., Sigma, St. Louis, Mo., U.S.A., catalogue No. p4914 "Proteinase K"). Various treatment conditions using protease K have been found useful. It is preferred that a high concentration of protease K (e.g., 1.5–2.5 mg/ml) be used for short (5–10 minutes) incubation periods to completely degrade cellular and viral protein and expose viral nucleic acid for amplification. When lower concentrations of protease K (e.g., 0.5 mg/ml) are used, longer incubation periods (30–60 minutes) are required to achieve the same effect. Other lysis approaches are also contemplated, including lysis by heating.

The present invention also contemplates labelling methods wherein the oligonucleotide probe sequences have at least one label attached or integrated into its structure. Labels are generally intended to facilitate the detection of the virus. Labels are chosen from the group consisting of enzymes, fluorophores, high-affinity conjugates, chemiphores and radioactive atoms ("radiolabels"). While other labels may be used, the present invention contemplates: 1) the enzymes alkaline phosphatase, β-galactosidase and glucose oxidase; 2) the affinity conjugate system of biotin-avidin; 3) the fluorophore that is fluorescein; 4) the chemiphore that is luminol; and 5) the preferred radiolabels $^3$H, $^{14}$C and $^{32}$P.

It is not intended that the present invention be limited by the nature of the label used. The present invention contemplates single labelling (e.g., a radiolabel, a fluorophore, etc.) and double labelling (e.g., two radiolabels, a radiolabel and a fluorophore, etc.).

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); mM (millimolar); µM (micromolar); mmol (millimoles); µg (micrograms); ml (milliliters); µl (microliters); cm (centimeters); mm (millimeters); bp (base pair); °C. (degrees Centigrade); s (seconds); Ci (Curies); µCi (microCuries); cpm (counts per minute); rpm (revolutions per minute); DTT (dithiothreitol); EDTA (ethylenediamine-tetracetic acid); SDS (sodium dodecyl sulfate); Tris (tris(hydroxymethyl)aminomethane); NaCl (sodium chloride); KCl (potassium chloride); MgCl$_2$ (magnesium chloride); dNTP (indicates a mixture of dATP, dTTP, dCTP and dGTP); PAGE (polyacrylamide gel electrophoresis); V (volts); W (watts); mA (milliamps); DNEN (Dupont-New England Nuclear, Boston, Mass.).

Generally, PCR was carded out using approximately 200 µM dNTPs (deoxyribonucleotide 5'-triphosphates) and approximately 0.5 µM primers. Five Units/100 µl of *Taq* polymerase was used. PCR reactions were overlaid with approximately 30 tl light mineral oil. A typical PCR for HIV amplification using a Perkin-Elmer Cetus DNA Thermal Cycler (Part No. N8010150) was: denaturation at 95° C. for 30 seconds; annealing at 55° C. for 30 seconds; and extension at 72° C. for 1 minute. PCR cycles were normally carded out in this manner for 35 cycles.

Amplification of HIV sequences was performed using the primer pair SK38 (SEQ ID NO: 1)/SK39 (SEQ ID NO:2). These primers bound a 115 nucleotide sequence (SEQ ID NO:3) present in HIV nucleic acid sequences. Amplification of HIV target sequences using the SK38 (SEQ ID NO:1)/SK39 (SEQ ID NO:2) primer pair yields a 115 bp product (SEQ ID NO.3). The sequences of the SK38 (SEQ ID NO:1) and SK39 (SEQ ID NO:2) primers and the 115 nucleotide HIV target (SEQ ID NO:3) are shown in FIG. 2.

Amplified products were analyzed by liquid oligomer hybridization (OH), using a $^{32}$P-end-labelled oligonucleotide named SK19 (SEQ ID NO:4). SK19 (SEQ ID NO:4) is specific for the p24 gag gene region of HW which is bounded by SK38 (SEQ ID NO:1)/SK39 (SEQ ID NO:2). The sequence of SK19 (SEQ ID NO:4) is shown in FIG. 2. The hybrids were separated from unincorporated probe by PAGE on a non-denaturing gel.

The procedure for end labelling of probes is as follows. Probes were end-labeled with γ-$^{32}$P-ATP by T$_4$ polynucleotide kinase. Typically, 0.2 µg of an oligonucleotide probe was incubated with 20 µCi γ-$^{32}$P-ATP (6000 Ci/mmol, DNEN) and 20 units of T$_4$ polynucleotide kinase (New England BioLab) at 37° C. for one hour. After stopping the reaction with 25 mM EDTA, the labeled probe was separated from unincorporated γ-$^{32}$P-ATP by spin column chromatography. A mini-sephadex G-50 column (1 ml) was packed by centrifugation (2 minutes, 1,800 rpm in a table top centrifuge) in a 1 ml disposable syringe in TE buffer. The T$_4$ kinase reaction products were loaded on the top of the column and centrifuged again at 1,800 rpm for 2 minutes. The labeled probe was collected in the exclusion volume.

Where polyacrylamide gel electrophoresis (PAGE) was used, non-denaturing 12% acrylamide gels were poured. Samples were loaded in 10 mM Tris, 10 mM EDTA, 0.1% SDS, 10% glycerol, 0.025% tracking dyes (bromphenol blue and xylene cyanol), then electrophoresed for approximately 30–45 minutes at 200 V, 50 W, 25 mA. Following PAGE, individual bands were visualized by autoradiography involving exposure for one hour at 4° C. to Kodak XAR-5 films with an intensifying screen.

The following examples are provided in order to demonstrate and further illuminate certain aspects of the practice of the invention.

EXPERIMENT 1

Detection Of HIV-1 Sequences In Cells From Hair Root

Three hairs were pulled from a seropositive patient who had developed AIDS and were collected in a sterile 15 ml plastic conical tube. The hair follicles were cut with scissors and transferred into a 1.5 ml Eppendorf tube. To the hair follicles, 10 of lysis buffer (10 mM Tris-HCl pH 8.0, 1 mM EDTA, 0.5% Tween 20 (polyoxyethylenesorbitan monolaurate), 0.5% Nonidet P-40 (NP-40, 0.05% proteinase K) was added and incubated at 55° C. for 30 min. After lysis, proteinase K was inactivated by heating at 95° C. for 20 min, and the lysate was centrifuged at 12,000 rpm for 5 min. The supernatant was collected for PCR. PCR was carried out for 35 cycles in a 10 or 20 µl reaction containing 5.0 µl of the cell lysate, 50 mM Tris-HCl, pH 8.5, 50 mM KCl, 2.5 mM MgCl$_2$, 200 µg/ml gelatin, 0.5 gM primer pair SK38 (SEQ ID NO:1) SK39 (SEQ ID NO:2), 1 unit of *Taq* polymerase (Perkin-Elmer Cetus, Norwalk, Conn.). The PCR cycling scheme was as follows: 95° C. for 30 s, 55° C. for 30 s, and 72° C. for 1 min in a Perkin-Elmer Cetus thermocycler. A hair plucked from a HIV-1 seronegative person as a negative control was processed in parallel in the same procedure. A series of dilutions of the HIV sequence-containing plasmid, pBKBH10S, with known copies, were amplified for quantitation. The PCR products were analyzed by liquid oligomer hybridization. Y. S. Zhu et al., The San Diego Conference on Nucleic Acids Abstract, p. 5. (1990); Y. S. Zhu et al., VIII International Conference on AIDS—Amsterdam, Abstract, p. 2111 (1992).

The method of liquid oligomer hybridization is as follows. To 10 82 1 of the PCR product, 3.3 µl of $^{32}$p end-labelled SK19 (SEQ ID NO:4) (5–10×10$^5$ cpm in 40 mM EDTA, 60 mM NaCl) specific for the p24 gag gene region bounded by SK38 (SEQ ID NO: 1)/SK39 (SEQ ID NO:2) is added. The mix is heated at 95° C. for 5 min and hybridized at 55° C. for 15 min. The hybridized SK19 (SEQ ID NO:4)/PCR product complex is identified by separation on a 12% polyacrylamide gel and exposure to X-ray film with an intensifying screen for 1 hr at 4° C. The bands corresponding to the 115 bp HIV-1 sequence (SEQ ID NO:3) in the gel are quantitated with an Ambis Radioanalytic Imaging System.

The results are shown in FIG. 3A. While the HIV-1 seronegative person tested negative by PCR (lane 1), the HIV-1 seropositive person tested positive for HIV-1 DNA by PCR when two different concentrations of hair cell lysate were tested (low, lane 2 and high, lane 3). Based on the HIV-1 DNA standards (copy number as indicated in FIG. 3A), approximately 200 copies of HIV-1 DNA were present in the cells from 3 hair follicles.

EXPERIMENT 2

Comparison Of HIV-1 Seronegative And Seropositive Persons

Figure 3B:
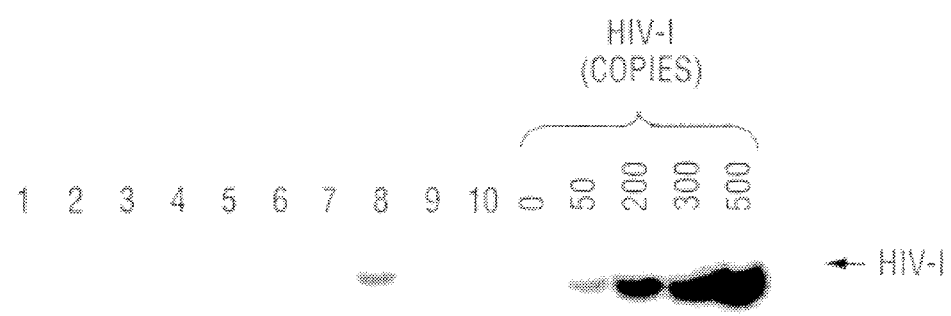
FIG. 3B is an autoradiogram of PCR products following liquid oligomer hybridization with the $^{32}$P-labelled SK19 (SEQ ID NO:4) probe which demonstrates the presence of HIV sequences in HIV seropositive persons and the absence of HIV sequences in HIV seronegative persons.

Eight HIV-1 seronegative persons and two HIV-1 seropositive persons were chosen for this blind test. The methods used were essentially the same as in Experiment 1. Approximately three hairs were plucked from each person. Cell lysates were made from individual hairs as described. The results of the amplification of HIV sequences in the samples are shown in FIG. 3B. All of the eight HIV-1 seronegative persons (Lanes 1, 2, 3, 4, 6, 7, 9 and 10) were HIV-1 DNA negative by PCR. One HIV-1 seropositive patient (8) was positive for hair follicle HIV-1 DNA by PCR. It is estimated that the one hair follicle had about 50 copies of HIV-1 DNA.

One of the two HIV-1 seropositive patients, (5), was HIV-1 DNA negative by PCR. In order to explain this result, a second sample of the PCR product from this individual was hybridized to an oligonucleotide probe specific for HLA sequences. The sample tested negative for the presence of HLA sequences. Since HLA sequences are present in the genomic DNA of every nucleated cell, this indicates that no PCR-amplifiable DNA was obtained from this hair sample at the outset, which is why no HIV-1 DNA was detected.

During sample preparation, it was noted that the hair from (5) did not appear to have a root. This observation was confirmed by microscopic examination of the hair sample. This underscores the need to obtain plucked hair that contains hair follicle cells and to properly separate the hair follicle from the hair shaft for analysis.

EXPERIMENT 3

Quantitation Of HIV-1 RNA In Hair Follicle

In order to determine if virus expression and active production of virus takes place in the hair follicle, its HIV-1 RNA is tested by RT-PCR. The hair follicles are lysed in 10 µl of RNAzol in the presence of 2 µg yeast tRNA as carrier and 80 µl of chloroform is added. After phase separation, total RNA in the aqueous phase is precipitated with alcohol (e.g., isopropanol). Total RNA is reverse transcribed in 20 µl containing 50 mM Tris-HCl pH 8.3, 150 mM KCl 10 mM $MgCl_2$, 10 mM DTT, 200 µM dNTPs, 0.1 µM hexamer, 20 units RNasin, (Promega), and 5 units reverse transcriptase (Seikagaku America, Inc.) at 37° C. for 30 min. After inactivation of the reaction by heating, the cDNA is amplified by PCR as described in Experiment 1. A synthetic HIV-1 RNA standard (50–1000 copies) is concurrently amplified by RT-PCR for quantitation. If the hair follicle shows HIV-1 RNA positive by RT-PCR, then copy number of HIV-1 RNA per hair follicle is determined by comparison to the HIV RNA standard.

From the above, it is apparent that the present invention provides a method for detecting HW nucleic acid sequences in hair follicle cells. Sample collection and storage is uncomplicated and inexpensive with this technique. In addition, the hair follicle cell assay avoids the invasive procedure of venipuncture and the need for trained personnel to draw blood. The patients plucked their own hairs and provided them as samples in the experiments described. The hair follicle cell assay is a rapid and sensitive test for HIV infection and avoids the safety problems of technicians handling HIV-contaminated blood.

All patent publications cited in this specification are herein incorporated by reference as if each individual publication were specifically and individually indicated to be incorporated by reference.

I claim:

1. A method for detecting a viral nucleic acid sequence from the human immunodeficiency virus in a sample of hair comprising the steps of:
   a) providing cells from at least one hair follicle, said cells suspected of containing a viral nucleic acid sequence from the human immunodeficiency virus;
   b) amplifying said viral nucleic acid sequence from the human immunodeficiency virus in said hair follicle; and
   c) detecting said viral nucleic acid sequence.

2. The method of claim 1 wherein said vital nucleic acid sequence is DNA.

3. The method of claim 1 wherein said vital nucleic acid sequence is RNA.

4. A method for detecting a human immunodeficiency virus infection comprising the steps of:
   a) providing cells from at least one hair follicle suspected of containing an HIV nucleic acid sequence:
   b) lysing said cells to make a lysate containing said nucleic acid;
   c) treating said lysate to amplify said HIV nucleic acid sequence; and
   d) detecting said HIV nucleic acid sequence.

5. A method for detecting a human immunodeficiency virus infection as in claim 4 wherein said lysing in step (b) comprises adding a lysing agent.

6. A method for detecting a human immunodeficiency virus infection as in claim 5 wherein said lysing agent comprises a protease.

7. A method for detecting a human immunodeficiency virus infection as in claim 6 further comprising the step of inactivating said protease.

8. A method for detecting a human immunodeficiency virus infection as in claim 4 wherein step (c) comprises:
   a) providing in any order:
      i) all standard reagents necessary to amplify at least a portion of said human immunodeficiency virus nucleic acid sequence, and
      ii) at least one amplification enzyme capable of initiating an amplification reaction resulting in a nucleic acid product,
   b) adding said reagents so as to form a reaction mixture, and
   c) adding said amplification enzyme to said reaction mixture.

9. The method of claim 8 wherein said amplification enzyme is *Thermus aquaticus* polymerase.

10. A method for detecting a viral nucleic acid sequence from the human immunodeficiency virus in a sample of hair comprising the steps of:
    a) providing cells from at least one hair follicle suspected of containing a viral nucleic acid sequence from the human immunodeficiency virus;
    b) lysing said cells with a protease to make a lysate containing said viral nucleic acid sequence:
    c) inactivating said protease:
    d) treating said lysate to amplify said viral nucleic acid sequence; and
    e) detecting said viral nucleic acid sequence.

11. The method of claim 10 wherein said viral nucleic acid sequence is DNA.

12. The method of claim 10 wherein said viral nucleic acid sequence is RNA.

13. The method of claim 10 wherein step (d) comprises:
    a) providing in any order:
       i) all standard reagents necessary to amplify at least a portion of said viral nucleic acid sequence, and
       ii) at least one amplification enzyme capable of initiating an amplification reaction resulting in a nucleic acid product;
    b) adding said reagents so as to form a reaction mixture; and
    c) adding said amplification enzyme to said reaction mixture.

14. The method of claim 13 wherein said amplification enzyme is *Thermus aquaticus* polymerase.

* * * * *

UNITED STATES PATENT AND TRADEMARK OFFICE
CERTIFICATE OF CORRECTION

PATENT NO. : 5,512,430
DATED : April 30, 1996
INVENTOR(S) : Yu Gong

Page 1 of 5

It is certified that error appears in the above-indentified patent and that said Letters Patent is hereby corrected as shown below:

On the Title page, item [54] and column 1, line 1;

please delete "DIAGNOSTIC ARRAY FOR VIRUS INFECTION" and insert --DIAGNOSTIC ASSAY FOR VIRUS INFECTION--.

UNDER THE HEADING "OTHER PUBLICATIONS":

Please delete "Sigma, St. Louis, MO, U.S.A., Catalogue No. p4914 "Proteinase K."
M. Piatak, Jr., et al., "High Levels of HIV-1 in Plasma During All Stages of Infection Determined by Competitive PCR," Science 259:1749 (1993)." and insert --Sigma, St. Louis, MO, U.S.A., Catalogue No. p4914 "Proteinase K." M. Piatak, Jr., et al., "High Levels of HIV-1 in Plasma During All Stages of Infection Determined by Competitive PCR," Science 259:1749 (1993)--.

In column 1, line 1, please delete "ARRAY" and insert --ASSAY--.

In column 1, line 23, please delete "gag-pol-env" and insert --*gag-pol-env*--.

UNITED STATES PATENT AND TRADEMARK OFFICE
CERTIFICATE OF CORRECTION

PATENT NO. : 5,512,430
DATED : April 30, 1996
INVENTOR(S) : Yu Gong

It is certified that error appears in the above-indentified patent and that said Letters Patent is hereby corrected as shown below:

In column 1, line 42, please delete "697, col 1" and insert --699, Col. 1--.

In column 1, line 50, please delete "Abtract" and insert --Abstract--.

In column 1, line 54, following "1094, please insert --, Abstract--.

In column 1, line 59, following "295", please insert --,--.

In column 1, line 60, please delete "Ratnet" and insert --Ratner--.

In column 2, line 48, please delete "Stiles" and insert --Stites--.

In column 3, line 57, please delete "imxnuno" and insert --immuno--.

In column 4, line 58, following "(1990)" please insert --at p. 1210, Abstract--.

In column 5, line 2, please delete "9. 979" and insert --979--.

In column 5, line 17, please delete "183" and insert --543--.

UNITED STATES PATENT AND TRADEMARK OFFICE
CERTIFICATE OF CORRECTION

PATENT NO. : 5,512,430
DATED : April 30, 1996
INVENTOR(S) : Yu Gong

It is certified that error appears in the above-indentified patent and that said Letters Patent is hereby corrected as shown below:

In column 5, line 18, please delete "col 1" and insert --Abstract--.

In column 5, line 64, please delete "p. 853 Abstract" and insert --p.3042, Col. 1--.

In column 6, line 6, following "(1989)" please insert --at p. 560, Abstract--.

In column 7, line 17, please delete "carded" and insert --carried--.

In column 7, line 26, please delete "carded" and insert --carried--.

In column 7, line 39, please delete "gag" and insert --*gag*--.

In column 7, line 39, please delete "HW" and insert --HIV--.

In column 8, line 11, following "10" please insert --$\mu$l--.

In column 8, line 13, please delete "P- 40" and insert --P-40--.

In column 8, line 13, please delete "(NP-40," and insert --(NP-40),--.

In column 8, line 20, please delete "0.5 gM" and insert --0.5 $\mu$M--.

UNITED STATES PATENT AND TRADEMARK OFFICE
CERTIFICATE OF CORRECTION

PATENT NO. : 5,512,430
DATED : April 30, 1996
INVENTOR(S) : Yu Gong

It is certified that error appears in the above-indentified patent and that said Letters Patent is hereby corrected as shown below:

In column 8, line 21, please delete "ID NO:1) SK39" and insert --ID NO:1)/SK39--.

In column 8, line 22, please delete "Conn.)" and insert --CT)--.

In column 8, line 35, please delete "10 82 1" and insert --10 $\mu$l--.

In column 8, line 37, please delete "gag" and insert --*gag*--.

In column 10, line 2, following "KCl" please insert --,--.

IN THE CLAIMS:

In column 11, line 35, please delete "vital" and insert --viral--.

In column 11, line 37, please delete "vital" and insert --viral--.

In column 11, line 42, please delete "sequence:" and insert --sequence;--.

In column 12, line 39, please delete "sequence:" and insert --sequence;--.

UNITED STATES PATENT AND TRADEMARK OFFICE
CERTIFICATE OF CORRECTION

PATENT NO. : 5,512,430
DATED : April 30, 1996
INVENTOR(S) : Yu Gong

It is certified that error appears in the above-indentified patent and that said Letters Patent is hereby corrected as shown below:

In column 12, line 40, please delete "protease:" and insert --protease;--.

Signed and Sealed this

Twenty-first Day of January, 1997

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATAATCCACC TATCCCAGTA GGAGAAAT 28

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTTGGTCCTT GTCTTATGTC CAGAATGC 28

( 2 ) INFORMATION FOR SEQ ID NO:3:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATAATCCACC TATCCCAGTA GGAGAAATTT ATAAAGATG GATAATCCTG GGATTAAATA    60

AAATAGTAAG AATGTATAGC CCTACCAGCA TTCTGGACAT AAGACAAGGA CCAAA    115

( 2 ) INFORMATION FOR SEQ ID NO:4:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

ATCCTGGGAT TAAATAAAAT AGTAAGAATG TATAGCCCT    39